United States Patent

Petigara et al.

Patent Number: 5,137,899
Date of Patent: Aug. 11, 1992

[54] BROMATE AS INHIBITOR OF NITROSAMINE FORMATION FOR NITRATE STABILIZED ISOTHIAZOLONES AND PROCESS

[75] Inventors: Ramesh B. Petigara, Hatfield; Edward S. Lashen, Furlong, both of Pa.

[73] Assignee: Rohm and Haas Company, Philadelphia, Pa.

[21] Appl. No.: 785,586

[22] Filed: Oct. 30, 1991

[51] Int. Cl.$^5$ .................... A01N 43/80; C07D 275/00
[52] U.S. Cl. ........................................ 514/372; 71/67; 548/213
[58] Field of Search ........................ 548/213; 514/372; 71/67

[56] References Cited

U.S. PATENT DOCUMENTS

| | | | |
|---|---|---|---|
| 3,849,430 | 11/1974 | Lewis et al. | 548/213 |
| 3,870,795 | 3/1975 | Miller et al. | 548/213 |
| 4,067,878 | 1/1978 | Miller et al. | 548/213 |
| 4,539,266 | 9/1985 | Miyazaki | 548/213 |
| 4,824,957 | 4/1989 | Amick | 548/213 |
| 4,939,266 | 7/1990 | Bayer et al. | 548/213 |

Primary Examiner—Joseph Paul Brust
Assistant Examiner—M. S. H. Gabilan
Attorney, Agent, or Firm—Michael B. Fein

[57] ABSTRACT

An improved process for preparing a 3-isothiazolone of the formula

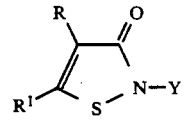

wherein
R and $R^1$ are independently selected from hydrogen, halogen or R is a ($C_1$-$C_4$) alkyl group and $R^1$ is a halogen; Y is hydrogen, a ($C_1$-$C_{18}$) alkyl group, an unsubstituted or halo-substituted ($C_2$-$C_8$) alkenyl or alkynyl, a cycloalkyl or substituted ($C_3$-$C_{12}$) cycloalkyl, an aralkyl or halo-, ($C_1$-$C_4$) alkyl-, or ($C_1$-$C_4$) alkoxy-substituted aralkyl of to 10 carbon atoms, or an aryl or halo-, ($C_1$-$C_4$) alkyl-, or ($C_1$-$C_4$) alkoxy-substituted aryl aryl group of up to 10 carbon atoms; comprising
(a) reacting a disulfide ester with an amine to generate a disulfide amide;
(b) contacting the disulfide amide with a halogenating agent in order to cyclize the amide to form the isothiazolone.HX;
(c) neutralizing the isothiazolone.HX;
(d) stabilizing the neutralized isothiazolone by adding a metal nitrate;
(e) a heat treatment step the improvement comprising adding prior to step (e), after step (c) and before, during or after step (d), an amount of a metal bromate.

Compositions resulting from the above process are disclosed.

15 Claims, No Drawings

BROMATE AS INHIBITOR OF NITROSAMINE FORMATION FOR NITRATE STABILIZED ISOTHIAZOLONES AND PROCESS

BACKGROUND OF THE INVENTION

1. Field of the Invention

This invention is directed to an improved process for the preparation of nitrate stabilized 3-isothiazolone compounds substantially free of nitrosamine.

2. Description of the Prior Art

3-Isothiazolones have generated high commercial interest as microbicides to prevent spoilage of certain aqueous and non-aqueous products caused by microorganisms. Isothiazolones are highly effective microbicides (as used herein, "microbicides" includes bactericides, fungicides and algicides and microbicidal activity is intended to include both the elimination of and the inhibition or prevention of growth of microbial organisms such as bacteria, fungi and algae); by suitable choice of functional groups, they are useful in a broad range of applications. These compounds may be represented by the following general formula:

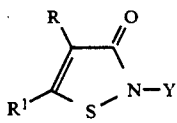

wherein R and $R^1$ are independently selected from hydrogen, halogen or a ($C_1$–$C_4$) alkyl group; Y is hydrogen, a ($C_1$–$C_{18}$) alkyl group, an unsubstituted or halo-substituted alkenyl or alkynyl of 2 to 8 carbon atoms, a cycloalkyl or substituted cycloalkyl of 3 to 12 carbon atoms, an aralkyl or halo-, ($C_1$–$C_4$) alkyl-, or ($C_1$–$C_4$) alkoxy-substituted aralkyl of up to 10 carbon atoms, or an aryl or halo-, ($C_1$–$C_4$) alkyl-, ($C_1$–$C_4$) alkoxy-substituted aryl group of up to 10 carbon atoms.

Unfortunately, solutions of the 3-isothiazolones, especially aqueous solutions or solutions in polar organic solvents such as alcohols containing trace to significant amounts of water, are unstable, leading to reduced biological effectiveness.

This is especially true of the 5-halogen containing 3-isothiazolones, where Y above is a $C_1$–$C_8$ alkyl, an aralkyl of up to 10 carbon atoms or a cycloaliphatic radical. The instability results from an opening of the isothiazolone ring to form linear compounds which do not have the same biological properties as the ring compounds. U.S. Pat. Nos. 3,870,795 and 4,067,878 teach that in order to inhibit ring cleavage, nitrate salts, for example, those of metals such as barium, cadmium, calcium, chromium, cobalt, copper, iron, lead, lithium, magnesium, manganese, nickel, silver, sodium, strontium, tin and zinc, can be added to isothiazolone solutions. These patents also teach that other common metal salts, including chlorates and perchlorates, are ineffective in stabilizing solutions of isothiazolones. Thus it is commercially desirable today to formulate many of the 5-hologenated 3-isothiazolone biocides either alone or in combination with other 3-isothiazolone biocides in solutions containing water or organic solvent or mixtures thereof together with nitrate stabilizers to prevent decomposition of the 3-isothiazolone.

One of the existing commercial processes used for manufacturing the 3-isothiazolones includes amidation of a disulfide ester followed by the halogen induced cyclization of the amide:

AMIDATION

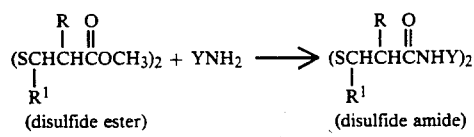

CYCLIZATION

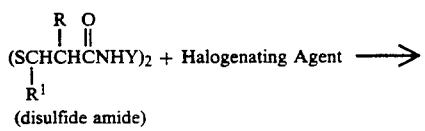

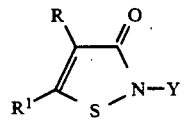

wherein $R^1$ is hydrogen and R is hydrogen or ($C_1$–$C_4$) alkyl and Y is as set forth in the above general formula. Such processes for the manufacture of 3-isothiazolones are described in U.S. Pat. Nos. 3,849,430 and 4,939,266.

Cyclization is accomplished by contacting the amide with a halogenating agent. Typical halogenating agents include chlorine, bromine, sulfuryl chloride, sulfuryl bromide, N-chlorosuccinimide, N-bromosuccinimide, and the like. Chlorine and sulfuryl chloride are the preferred halogenating agents. Isothiazolone hydrohalide salts (isothiazolone.HX) are generated in the halogenation/cyclization step of the process. The isothiazolone.HX cake is washed and can be reslurried or dissolved in the same or different solvent. In organic systems, a neutralizing agent such as an organic amine is added (see U.S. Pat. No. 4,824,957) and in aqueous systems, a neutralizing agent such as magnesium oxide or calcium oxide is added to yield the free base isothiazolone and a halide salt.

It is known that certain 3-isothiazolone biocides produced using the prior art disulfide intermediate contain by-product impurities having a secondary or tertiary amine which, upon exposure to nitrosating conditions, can be converted to nitroso compounds (see U.S. Pat. No. 4,539,266).

The amidation reaction above produces a mixture containing about 95% mono-, di-, and tri-thioamides and methanol. Upon cleavage of the disulfide (during amidation), N-methylacrylamide (in the case where Y is methyl) by-product is believed to be formed. Conjugate addition of monomethylamine (Y=methyl) to this cleavage by-product leads to the formation of the principal nitrosamine precursor, N-methyl-3-(N'-methylamino)propionamide (MMAP) by the following reaction:

MMAP produced by the above reaction can also add to N-methyl-acrylamide according to the following equation:

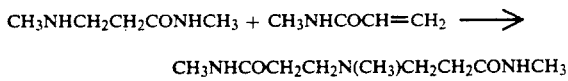

Both of the above nitrosamine precursors have been identified as being present in the intermediate disulfide amide produced when amidating the disulfide ester starting material. The nitrosamine precursors remain with the AI through chlorination, neutralization and formulation of the 3-isothiazolone composition until the nitrate salt is added, at which time nitrosation takes place (principally during heat treatment) to form a nitrosamine, e.g.:

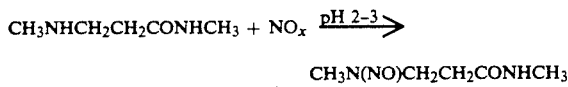

As a group, nitroso compounds are generally suspected to be possible carcinogens. Accordingly, it is desirable to find means for eliminating even the trace quantities of those by-product impurities which serve as precursors to the formation of nitrosamines, especially for products to be used in applications where human or animal contact is anticipated.

The nitrosamine problem is exacerbated when formulating 3-isothiazolone compositions in solutions, either aqueous solutions or organic solutions or mixtures thereof wherein it is necessary to incorporate a nitrate salt, see, e.g., U.S. Pat. No. 4,067,878. When the metal nitrate salt is present as a stabilizer, the by-product secondary or tertiary amine compound present in the 3-isothiazolone reaction mixture is subject to being nitrosated to a nitroso compound which may be suspected to be carcinogenic. The expression "nitrosamine precursor", or simply "precursor", is intended to identify a secondary amine (and if present, a tertiary amine) byproduct compound which can be converted to a nitrosamine.

SUMMARY OF THE INVENTION

It is an object of the present invention to provide an improved process to produce 3-isothiazolones having decreased levels of nitrosamine. A further object of the invention is a composition or solution of 3-isothiazolones prepared by the above process.

These objects and others which will become apparent from the following disclosure are achieved by the present invention which comprises in one aspect an improved process for preparing a 3-isothiazolone of the formula

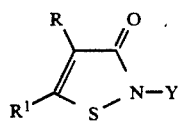

wherein
R and $R^1$ are independently selected from hydrogen, halogen or R is a $(C_1-C_4)$ alkyl group and $R^1$ is a halogen;
Y is hydrogen, a $(C_1-C_{18})$ alkyl group, an unsubstituted or halo-substituted alkenyl or alkynyl of 2 to 8 carbon atoms, a cycloalkyl or substituted cycloalkyl of 3 to 12 carbon atoms, an aralkyl or halo-, $(C_1-C_4)$ alkyl-, or $(C_1-C_4)$ alkoxy-substituted aralkyl of up to 10 carbon atoms, or an aryl or halo-, $(C_1-C_4)$ alkyl-, or $(C_1-C_4)$ alkoxy-substituted aryl group of up to 10 carbon atoms; comprising (a) reacting a disulfide ester with an amine to generate a disulfide amide;
(b) contacting the disulfide amide with a halogenating agent in order to cyclize the amide to form the isothiazolone.HX;
(c) neutralizing the isothiazolone.HX;
(d) stabilizing the neutralized isothiazolone by adding a metal nitrate;
(e) a heat treatment step the improvement comprising adding prior to step (e), after step (c) and before, during or after step (d), an amount of a metal bromate.

Representative Y substituents include methyl, ethyl, propyl, isopropyl, butyl, hexyl, octyl, cyclohexyl, 4-methoxyphenyl, 4-chlorophenyl, 3,4-dichlorophenyl, benzyl, 4-methoxybenzyl, 4-chlorobenzyl, phenethyl, 2-(4-chlorophenyl)ethyl, 4-phenylbutyl, hydroxymethyl, chloromethyl, chloropropyl, hydrogen, and the like.

By a substituted alkyl group is meant an alkyl group having one or more of its hydrogen atoms replaced by another substituted group. Examples of the substituted alkyl groups which characterize 3-isothiazolones of this invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazonylalkyl, and the like.

By a substituted aralkyl group is meant an aralkyl group having one or more of the hydrogen atoms on either the aryl ring or the alkyl chain replaced by another substituent group. Examples of the substituent aralkyl groups which characterize 3-isothiazolones of this invention include halogen-, $(C_1-C_4)$ alkyl, or $(C_1-C_4)$ alkoxy-substituted aralkyl groups, and the like.

By a substituted aryl group is meant an aryl group, such as benzene or naphthalene, having one or more of the hydrogen atoms on the aryl ring replaced by another substituent group. Examples of such substituent groups include halogen, nitro, $(C_1-C_4)$ alkyl, $(C_1-C_4)$ alkyl-acylamino, $(C_1-C_4)$ carbalkoxy, sulfamyl, and the like.

DETAILED DESCRIPTION OF THE INVENTION AND THE PREFERRED EMBODIMENTS

The process of the invention comprises adding to a process of preparation of 3-isothiazolones comprising amidation of a disulfide ester followed by halogenation-cyclization, neutralization, stabilizer addition and heat treatment, an amount of a metal bromate before, during or after the stabilizer addition, but prior to heat treatment to reduce the level of nitrosamine formation.

The amidation reaction is carried out in either aqueous or an organic solvent, either aliphatic or aromatic mixtures thereof. Illustrative of the solvents used are methanol and toluene. Toluene is preferred.

The preferred disulfide is dimethyl-3,3'-dithiodipropionate.

The halogenation-cyclization is conducted in an organic solvent, typically aromatic hydrocarbons, aliphatic hydrocarbons, chlorinated aromatic hydrocarbons, chlorinated aliphatic hydrocarbons, acetate esters, glycol ethers and glycol ether acetate. The preferred solvents are toluene, monochlorobenzene, ethyl acetate and butyl acetate.

The preferred halogenating agents are chlorine and sulfuryl chloride.

Y is preferably hydrogen, methyl, ethyl, propyl, isopropyl, butyl, hexyl, octyl, benzyl, 4-methoxybenzyl, 4-chlorobenzyl, phenethyl, 2-(4-chlorophenyl)ethyl, and cyclohexyl.

The neutralization with an organic amine is preferably carried out in the same solvent as in the halogenation-cyclization step.

The neutallization in aqueous media is carried out by introducing a metal oxide. The preferred neutralizing agent is magnesium oxide or calcium oxide.

Subsequent to the neutralization step, a stabilizer is added to the technical isothiazolone solution. The preferred stabilizers are metal nitrates, and the preferred metal nitrate is magnesium nitrate.

Subsequent to stabilizing the isothiazolone by adding a metal nitrate, a heat treatment step is performed. Heat treatment is effective for removing or decomposing by-products. The preferred heat treatment time is 30 minutes and the preferred temperature range is 60°-80° C.

Preferably, the metal bromate is introduced in the process after the neutralization step and either before, during or after the stabilization step, but prior to any heat treatment step. Most preferably, the metal bromate is introduced in the process before or simultaneously with the metal nitrate stabilizer.

The metal bromate may be added to the reaction mixture either in solution or as a solid.

The preferred metal bromates are calcium bromate, cobalt bromate, lithium bromate, magnesium bromate, potassium bromate, sodium bromate, strontium bromate, and zinc bromate. The more preferred metal bromates are potassium bromate, sodium bromate, magnesium bromate and lithium bromate, and the most preferred is potassium bromate.

Preferred amounts of the metal bromate are from about 0.5 to 3.0% by weight based upon the formulation which comprises solvent, isothiazolone and nitrate stabilizer. The most preferred levels are from about 1.0 to 2.0% by weight.

The preferred 3-isothiazolones of this invention are 5-chloro-2-methyl-3-isothiazolone, and 4,5-dichloro-2-methyl-3-isothiazolone, 5-chloro-2-octyl-3-isothiazolone, 4,5-dichloro-2-octyl-3-isothiazolone, 5-chloro-2-p-chlorobenzyl-3-isothiazolone, 4,5-dichloro-2-cyclohexyl-3-isothiazolone and 5-chloro-2-cyclohexyl-3-isothiazolone.

As can be seen from the preceeding disclosure and the following examples, the process of the invention provides a unique, novel, useful and highly advantageous process for producing 3-isothiazolones with decreased levels of nitrosamines.

The following specific examples are presented to illustrate the various aspects of the present invention but are not to be construed as limitations thereof.

EXAMPLE 1 (COMPARATIVE)

Step 1: Amidation

Into a three-liter, 4-necked flask equipped with a mechanical stirrer, thermometer, gas dispersion tube and dry ice condeser with nitrogen inlet adapter, was placed dimethyl-3,3'-dithiopropionate (1,062.5 g, 4.46 mol), toluene (535.0 g) and methanol (55.0 g). The apparatus was purged with nitrogen and the mixture was cooled to 10° C. Monomethylamine (346.0 g, 11.14 mol) was added through the gas dispersion tube with stirring at 10°-20° C. over 2 hrs. After completing the monomethylamine addition, the mixture was stirred at 20° C. for 20 hrs to complete the reaction. A thick, pale yellow slurry was obtained. At this time the unreacted monomethylamine and methanol by-product were distilled from the mixture at ~100 mm Hg. The crude, dry N,N'-dimethyl-3,3'-dithiopropionamide intermediate (1,022.4 g, 97% yield) contained 11,000 ppm N-methyl-3-(N'-methyl)aminopropionamide.

A portion of the intermediate slurry was filtered, washed with toluene and dried. The dry intermediate contained 8,000 ppm of N-methyl-3-(N'-methyl)aminopropionamide.

Step 2: Chlorination

Preparation of a mixture of 5-chloro-2-methyl-4-isothiazoline-3-one hydrochliride and 2-methyl-4-isothazoline-3-one hydrochloride.

A one-liter 3-necked round bottom flask was equipped with an overhead agitator, a feed line (outlet) and a condenser with a drying tube. Into this flask, 635.8 g of a slurry of N,N'-dimethyl-3,3'-dithiopropionamide ("DD Amide") (with 8,000 ppm precursor) in toluene was placed and agitated.

A one-liter, 5-necked resin kettle (i.e. chlorinator) was equipped with an agitator, a fritted glass gas dispersion tube for $Cl_2$ inlet, a thermometer, a condenser attached to an off-gas scrubber, and a feed line-inlet for intermediate slurry. The kettle was jacketed for ice-water circulation. The cooling system maintained the chlorination batch at 25°-30° C. The chlorinator was charged with 108 g of toluene as a heel, and the agitator started.

The DD Amide slurry and $Cl_2$ were fed concurrently at a molar feed ratio of 5.2. Thus, 453 g of the slurry was charged over a 55-minute period at a rate of about 8.2 g/min., while 227 g of $Cl_2$ (gas) was fed at a rate of about 4.1 g/min., using a calibrated flowmeter.

Step 3: Filtration and Neutralization

To the above agitated chlorination slurry 20 g of water was added gradually. After 10 min. of agitation, the batch was allowed to settle, and the mother liquor was siphoned out using a dipstick. An additional 45 g of water was added, and additional mother liquor was removed.

To the hydrochloride wet cake was added 116 g of water. The mixture was neutralized to pH 4.5 by gradually adding an aqueous MgO slurry. The neutralized material was transferred to a separatory funnel and 469 g of an aqueous Tech grade was separated from the organic layer:

| Active Ingredient (Tech) | Wt % |
| --- | --- |
| 5-chloro-2-methyl-4-isothiazoline-3-one | 17.1 |
| 2-methyl-4-isothazoline-3-one | 5.5 |

Step 4: (Stabilization)

The pH of the above Tech was adjusted to 2.9 and 46.5 g of magnesium nitrate hexahydrate and 7.24 g of water were added to 100 g of the AI with agitation to give a solution with the following composition:

| Component | Nominal Conc., Wt % |
| --- | --- |
| Total AI | 15.2 |
| $Mg(NO_3)_2$ | 17.4 |

Step 5: Heat Treatment

The above formulated product was transferred to a 500 ml 3-necked round bottom flask equipped with an overhead agitator, a water-cooled condenser and a thermometer attached to a thermo-watch and pneumatic pot lifter assembly supporting a heating mantle.

The formulated product was heat-treated at 95° C. for 4 hrs. The product, 153.7 g, was filtered to remove any trace amounts of solids, and analyzed. Analysis:

| Components | Wt % |
| --- | --- |
| 5-chloro-2-methyl-4-isothiazoline-3-one | 10.7 |
| 2-methyl-4-isothazoline-3-one | 3.4 |
| Nitrosamine* | 1200 ppm |

*$CH_3N(NO)CH_2CH_2CONHCH_3$

EXAMPLES 2–4

These examples illustrate the nitrosamine inhibiting capability of the use of metal bromate according to the invention. The relative concentration of the active ingredient was determined by reverse phase high pressure liquid chromatography (HPLC), utilizing an ultraviolet detector. The relative concentration of potassium bromate was determined by titration (KI/starch vs. sodium thiosulfate).

EXAMPLE 2

Following steps 1,2 and 3 as in Example 1 above, the technical grade product was obtained.

Step 4

A 100 g portion of the above technical grade material was adjusted to pH 4.5, and to this were added 38.8 g of magnesium nitrate hexahydrate, 2.2 g of potassium bromate and 3.8 g of water, to yeild the formulation having the following nominal composition:

| Component | Nominal Conc. Wt % |
| --- | --- |
| 5-chloro-2-methyl-4-isothiazoline-3-one | 11.3 |
| 2-methyl-4-isothazoline-3-one | 3.7 |
| $KBrO_3$ | 1.5 |
| $Mg(NO_3)_2$ | 15.5 |

The above formulation was heat treated at 65° C. for 30 minutes, as described in Step 4 of Example 1, to yield the product with the following composition essentially free of N-methyl-3-(N'-methyl-N'-nitroso)aminopropionamide (MMNP), a nitrosamine:

| Component | Wt % |
| --- | --- |
| 5-chloro-2-methyl-4-isothiazoline-3-one | 11.2 |
| 2-methyl-4-isothazoline-3-one | 3.2 |
| $KBrO_3$ | 0.21 |
| MMNP | 2 ppm |

EXAMPLE 3

The experiment described in Example 2 above was repeated with the only difference being in the heat treatment temperature. The formulation described in Example 2 was heat treated at 80° C. for 30 minutes to give the product with the following composition:

| Component | Wt % |
| --- | --- |
| 5-chloro-2-methyl-4-isothiazoline-3-one | 11.2 |
| 2-methyl-4-isothazoline-3-one | 3.1 |
| $KBrO_3$ | 0.06 |
| MMNP | 0.9 ppm |

EXAMPLE 4

A 100 g portion of the above technical grade material from Example 1 was adjusted to pH 5.5, and to this were added 38.8 g of magnesium nitrate hexahydrate, 2.2 g of potassium bromate and 3.8 g of water to yield the formulation having the following nominal composition, essentially free of MMNP:

| Component | Wt % |
| --- | --- |
| 5-chloro-2-methyl-4-isothiazoline-3-one | 11.3 |
| 2-methyl-4-isothazoline-3-one | 3.3 |
| $KBrO_3$ | 1.5 |
| $Mg(NO_3)_2$ | 15.5 |

The above formulation was heat treated at 65° C. for 30 minutes, as described in Step 4 of Example 1, to yield the product with the following composition essentially free of N-methyl-3-(N'-methyl-N'-nitroso)aminopropionamide (MMNP), a nitrosamine:

| Component | Wt % |
| --- | --- |
| 5-chloro-2-methyl-4-isothiazoline-3-one | 11.3 |
| 2-methyl-4-isothazoline-3-one | 3.3 |
| $KBrO_3$ | 0.26 |
| MMNP | 7.8 ppm |

EXAMPLE 5

The pH of a batch of a 3:1 mixture of 5-chloro-2-methyl-4-isothiazoline-3-one and 2-methyl-4-isothiazoline-3-one, prepared as in Example 1, was adjusted to 4.5. This material was then formulated with 15.5% magnesium nitrate and 1.5% potassium bromate (98.5% pure). The formulated product was heat treated for 30 minutes at 70° C. The final product gave the following composition, essentially free of MMNP and DMNA (dimethylnitrosamine):

| Component | Wt % |
| --- | --- |
| 5-chloro-2-methyl-4-isothiazoline-3-one | 12.8 |

-continued

| Component | Wt % |
|---|---|
| 2-methyl-4-isothazoline-3-one | 2.1 |
| KBrO3 | 0.6 |
| Mg(NO3)2 | 14.8 |
| MMNP | 0.6 ppm |
| DMNA | <0.1 ppm |

EXAMPLE 6

The pH of a batch of a 3:1 mixture of 5-chloro-2-methyl-4-isothazoline-3-one and 2-methyl-4-isothazoline-3-one, prepared as in Example 1, was adjusted to 4.5. This material was then formulated with 15.5% magnesium nitrate and 1.5% potassium bromate (98.5% pure). The formulated product was heat treated for 30 minutes at 80° C. The final product gave the following composition, essentially free of MMNP and DMNA (dimethylnitrosamine):

| Component | Wt % |
|---|---|
| 5-chloro-2-methyl-4-isothazoline-3-one | 14.6 |
| 2-methyl-4-isothazoline-3-one | 3.1 |
| KBrO3 | 0.45 |
| Mg(NO3)2 | 14.4 |
| MMNP | 21 ppm |
| DMNA | <0.1 ppm |

EXAMPLE 7

The pH of three different batches (B1, B2 and B3) of a 3:1 mixture of 5-chloro-2-methyl-4-isothazoline-3-one and 2-methyl-4-isothazoline-3-one, prepared as in Example 1, were adjusted to 4.0–5.0. These materials were then formulated with 15.5% magnesium nitrate and 1.5% potassium bromate (98.5% pure). The formulated products were heat treated for 30 minutes at 80° C., and filtered through a 60-micron polypropylene filter cartridge. The final products gave the following composition, essentially free of MMNP and DMNA (dimethylnitrosamine):

| Component | Wt % B1 | B2 | B3 |
|---|---|---|---|
| 5-chloro-2-methyl-4-isothazoline-3-one | 10.8 | 12.3 | 11.9 |
| 2-methyl-4-isothazoline-3-one | 3.5 | 3.7 | 3.3 |
| KBrO3 | 0.73 | 0.74 | 0.56 |
| Mg(NO3)2 | 15.1 | 15.2 | 15.5 |
| MMNP (ppm) | 2.16 | 1.46 | 1.1 |
| DMNA (ppm) | <0.1 | <0.1 | <0.1 |

EXAMPLE 8

This example illustrates the nitrosamine inhibition capability of bromate during storage. The three batches from example 7 above as well as the material from Example 5 above (B4) were subjected to accelerated storage. These batches were monitored for MMNP formation and the analyses follow:

| | As made | | On Storage | | | |
|---|---|---|---|---|---|---|
| | | | 55° C./30 day | | 25° C./6 mon | |
| | % KBrO3 | MMNP* | % KBrO3 | MMNP* | % KBrO3 | MMNP* |
| B1 | 0.73 | 2.1 | 0.15 | 13.0 | 0.56 | 6.2 |
| B2 | 0.74 | 1.1 | 0.11 | 7.3 | 0.51 | 4.6 |
| B3 | 0.56 | 1.1 | 0 | 586 | 0.38 | 4.5 |
| B4 | 0.6 | 0.6 | 0 | 52.0 | 0.45 | 3.4 |

*MMNP is reported in ppm.

It can be seen from the above data that on storage the product remains quite low in MMNP nitrosamine, as long as bromate is present. Once the bromate is consumed, the precursor converts to MMNP nitrosamine due to the presence of nitrate which provides the nitrosating species (NOx).

While the invention has been described in sufficient detail for those skilled in the art to be able to make and use it, various alternatives, modifications, and improvements should become apparent from the foregoing disclosure without departing from the spirit and scope of the invention.

What is claimed is:

1. A process for preparing a biologically active, substantially nitrosamine free, metal nitrate salt-stabilized 3-isothiazolone compound of the formula

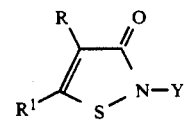

wherein R and R$^1$ are independently selected from the group consisting of hydrogen, halogen or R is a (C1–C4) alkyl and R$^1$ is a halogen; Y is an alkyl or substituted alkyl of 1 to 18 carbon atoms, an unsubstituted or halo-substituted alkenyl or alkynyl of 2 to 8 carbon atoms, a cycloalkyl or substituted cycloalkyl of 2 to 12 carbon atoms, an aralkyl or halo-, (C$_1$–C$_4$) alkyl-, or (C$_1$–C$_4$) alkoxy substituted aralkyl of up to 10 carbon atoms, or an aryl or halo-, (C$_1$–C$_4$) alkyl-, or (C$_1$–C$_4$) alkoxy-substituted aryl of up to 10 carbon atoms; comprising
   (a) reacting a disulfide ester with an amine to generate a disulfide amide;
   (b) contacting the disulfide amide with a halogenating agent in order to cyclize the amide to form the isothiazolone.HX;
   (c) neutralizing the isothiazolone.HX;
   (d) stabilizing the neutralized isothiazolone by adding a metal nitrate;
   (e) a heat treatment step the improvement comprising adding prior to step (e), after step (c) and before, during or after step (d), an amount of a metal bromate.

2. The process of claim 1 wherein said metal nitrate is a nitrate salt of a metal cation selected from the group consisting of barium, cadmium, calcium, chromium, cobalt, copper, iron, lead, lithium, magnesium, manganese, nickel, silver, sodium, strontium, tin and zinc.

3. The process of claim 1 wherein said metal bromate is a bromate salt of a metal cation selected from the group consisting of calcium, cobalt, lithium, magnesium, potassium, sodium, strontium, and zinc.

4. The process of claim 1 wherein the pH of said metal nitrate-stabilized 3-isothiazolone prior to the addition of said metal bromate is 3.0 or greater.

5. The process of claim 4 wherein said pH is 4.0 or greater.

6. The process of claim 1 wherein said metal nitrate is magnesium nitrate and said metal bromate is potassium bromate.

7. The process of claim 6 wherein said isothiazolone is selected from the group consisting of 5-chloro-2-methyl-3-isothiazolone, and 4,5-dichloro-2-methyl-3-isothiazolone, 5-chloro-2-octyl-3-isothiazolone, 4,5-dichloro-2-octyl-3-isothiazolone, 5-dichloro-2-p-chlorobenzyl-3-isothiazolone, 4,5-dichloro-2-cyclohexyl-3-isothiazolone and 5-chloro-2-cyclohexyl-3-isothiazolone.

8. The process of claim 7 wherein said pH is 4.0.

9. The process of claim 1 wherein the duration of said heat treatment step is 30 minutes and the temperature of said heat treatment step is between 60° and 80° C.

10. The process of claim 1 wherein said amount of metal bromate is from about 0.5 to 3.0% by weight.

11. The process of claim 10 wherein said amount of metal bromate is from about 1.0 to 2.0% by weight.

12. A composition comprising substantially nitrosamine free, metal nitrate salt-stabilized 3-isothiazolone prepared by the process of claim 1.

13. A composition according to claim 12 wherein said isothiazolone is selected from the group consisting of 5-chloro-2-methyl-3-isothiazolone, and 4,5-dichloro-2-methyl-3-isothiazolone, 5-chloro-2-octyl-3-isothiazolone, 4,5-dichloro-2-octyl-3-isothiazolone, 5-dichloro-2-p-chlorobenzyl-3-isothiazolone, 4,5-dichloro-2-cyclohexyl-3-isothiazolone and 5-chloro-2-cyclohexyl-3-isothiazolone.

14. A composition according to claim 13 wherein said metal nitrate is magnesium nitrate and said metal bromate is potassium bromate.

15. A composition according to claim 12 wherein said isothiazolone is a mixture of 2-methyl-3-isothiazolone and 5-chloro-2-methyl-3-isothiazolone.

* * * * *